United States Patent [19]

Kozbor et al.

[11] Patent Number: 4,693,975
[45] Date of Patent: Sep. 15, 1987

[54] HUMAN HYBRIDROMA FUSION PARTNER FOR PRODUCTION OF HUMAN MONOCLONAL ANTIBODIES

[75] Inventors: Danuta Kozbor; Carlo M. Croce, both of Philadelphia, Pa.

[73] Assignee: The Wistar Institute, Philadelphia, Pa.

[21] Appl. No.: 673,370

[22] Filed: Nov. 20, 1984

[51] Int. Cl.$^4$ .................. C12N 15/00; C12N 5/00; C12R 1/91
[52] U.S. Cl. .................. 435/172.2; 435/240.27; 435/948; 935/93; 935/100; 935/106
[58] Field of Search .................. 435/172.2, 240, 241, 435/948; 935/100, 93, 106

[56] References Cited

U.S. PATENT DOCUMENTS 4,529,694  7/1985  Lazarus et al. .................. 435/172.2
4,574,116  3/1986  Kaplan et al. .................. 435/948

FOREIGN PATENT DOCUMENTS 2079313  1/1982  United Kingdom .................. 435/240
2113715  8/1983  United Kingdom .................. 435/240

OTHER PUBLICATIONS

Pickering et al., "A Human Myeloma Cell Line that does not Express Immunoglobulin but Yields a High Frequency of Hybridomas", Journal of Immunology 129(1), pp. 406–412, (1982).
Littman et al., "Production of Human B-Cell Hybridomas from Patients with SLE", Arth. Rheum. 25(4), p. S28, (1982), Supp.
Shulman et al., "A Better Cell Line for Making Hybridomas Secreting Specific Antibodies", Nature 276, pp. 269–270, (1978).
Matsuoka et al., (1967), Proceedings of the Society for Experimental Biology and Medicine, 125: 1246–1250.
Kozbor et al., (1982), Proceedings of the National Academy of Sciences U.S.A., 79: 6651–6655.
Teng et al., (1983), Proceedings of the National Academy of Sciences U.S.A., 80: 7308–7312.
Milstein and Cuello, (1983), Nature, 305: 537–540.

Primary Examiner—John Edward Tarcza
Attorney, Agent, or Firm—Banner, Birch, McKie and Beckett

[57] ABSTRACT

Somatic cell hybrids of purely human origin are described that are suitable fusion partners for producing hybridomas by fusion with antibody producing cells, which hybridomas are stable and continuous.

12 Claims, No Drawings

HUMAN HYBRIDROMA FUSION PARTNER FOR PRODUCTION OF HUMAN MONOCLONAL ANTIBODIES

FIELD OF THE INVENTION

The present invention relates to a human somatic cell hybrid that exhibits a high fusion frequency with antibody producing cells including normal B lymphocytes. The present invention is specifically directed to a somatic cell hybrid produced by fusing a human lymphoblastoid cell with a human plasmacytoma cell.

BACKGROUND OF THE INVENTION

Several human lymphoblastoid cell lines and human myeloma cell lines have been suggested for fusion with human B lymphocytes. Fushion partners of purely human origin are particularly advantageous because the monoclonal antibodies produced by hybridomas prepared from such fusion partners and human B lymphocytes are more likely to be compatible with the natural human immune response system than antibodies produced by non-human or mixed hybridomas. Mouse-human hybridomas, for example, tend to lose their human chromosomes quite quickly, while hybridomas of human origin typically exhibit good stability with respect to human chromosomes.

Of available human myeloma fusion partners, the plasmacytomas have a well-established cell morphology characterized by abundant rough endoplasmic recticulum, numerous mitochondria and a well-developed Golgi appartus. Plasmacytomas also exhibit a high rate of immunoglobulin secretion. Unfortunately, plasmacytoma cells only rarely can be continuously maintained in vitro. Additionally, most plasmacytomas have doubling times between 36 and 73 hours and may require a plasmacyte-stimulating factor for proliferation in tissue culture. The frequency of hybrid formation using such cells also generally is quite low.

While available human lymphoblastoid cells exhibit higher fusion frequencies, are more easily maintained in tissue culture and have doubling times of about 20 to 30 hours, these cells do not have a well-developed rough endoplasmic recticulum and secrete much less immunoglobulin.

A purely human cell exhibiting some of the desirable characteristics of both plasmacytoma and lymphoblastoid cells would be particularly advantageous.

SUMMARY

It is an object of the present invention to provide a human hybrid myeloma fusion partner for production of human monoclonal antibodies.

Another object of the present invention is to provide a human somatic cell hybrid that exhibits a high fusion frequency with antibody producing cells such as normal lymphocytes so as to produce hybridomas which express antibodies compatible with the human immune response system.

A further object of the present invention is to provide a human somatic cell hybrid which can be used to produce hybridomas that secrete high levels of antibodies.

It is also an object of the present invention to provide a human somatic cell hybrid suitable for hybridization with human antibody producing B cells that expresses a selectable phenotype.

These and other objects are provided by the present invention which in one aspect comprises a stable, continuous human somatic cell hybrid cell line produced by fusing a mutant cell obtained from one of either the human plasmacytoma cell line RPMI 8226 or the human lymphoblastoid cell line GM-1500 with a cell obtained from the other of either the plasmacytoma cell line 8226 or the lymphoblastoid cell line GM-1500 to produce a first hybrid cell line, said mutant cell exhibiting a first selectable phenotype that can be complemented and a second selectable phenotype that can be transmitted upon fusion with said other cell, and then mutating a cell of said first hybrid cell line to obtain said human somatic cell hybrid cell line exhibiting a selectable phenotype that can be complemented upon fusion with an antibody producing cell and having the ability to form a stable, continuous cell line upon fusion with an antibody producing cell.

In another aspect, the present invention provides an antibody-secreting hybridoma cell resulting from the fusion of an antibody producing cell with a cell obtained from the above-identified human somatic cell hybrid cell line.

In still another aspect, the present invention pertains to a method for forming a stable, continuous human somatic cell hybrid cell line useful as a fusion partner with an antibody producing cell comprising fusing a mutant cell obtained from one of either the human plasmacytoma cell line RPMI 8226 or the lymphoblastoid cell line GM-1500 with a cell obtained from the other of either the RPMI 8226 cell line or the GM-1500 cell line to produce a first hybrid cell line, said mutant cell having a first selectable phenotype that can be complemented and a second selectable phenotype that can be transmitted upon fusion with said other cell, and then mutating a cell obtained from said first hybrid cell line to obtain a human somatic cell hybrid cell line having a selectable phenotype that can be complemented upon fusion with an antibody producing cell.

In a further aspect, the present invention pertains to a method for forming a hybridoma comprising fusing an antibody producing cell with a cell obtained from the above-identified human somatic cell hybrid cell line to obtain a cell hybrid of said antibody producing cell and said human somatic cell hybrid.

DETAILED DESCRIPTION

The present invention provides a stable, continuous human somatic cell hybrid cell line prepared by fusing a mutant obtained from one of either the human plasmacytoma cell line RPMI 8226 or the human lymphoblastoid cell line GM-1500 with a cell obtained from the other of either the RPMI 8226 cell line or the GM-1500 cell line to produce a first hybrid cell line and then mutating a cell of said first hybrid cell line to obtain a human somatic cell hybrid cell line exhibiting a selectable phenotype capable of being complemented upon fushion with an antibody producing cell. Such somatic cell hybrids possess the phenotypic characteristics of the plasmacytoma parental cell and exhibit a fusion frequency with antibody producing cells on the order of the lymphoblastoid parental cell. The somatic cell hybrid cell line of the present invention is useful as a fusion partner with antibody producing cells. The present invention also pertains to a method for preparing the somatic cell hybrid cell line.

The somatic cell line of this invention can be used to construct antibody secreting human hybridomas with human B cell lines generally. It has been hybridized with human B lymphocytes obtained from the peripheral blood of colorectal carcinoma patients as well as with human B cell lines immortalized by treatment with Epstein-Barr virus (EBV).

The human somatic cell hybrid of this invention is prepared by fusing a mutant cell obtained from one of either the human plasmacytoma cell line RPMI 8226 or the human lymphoblastoid cell line GM-1500 with a cell obtained from the other of either the RPMI 8226 cell line or the GM-1500 cell line. The human plasmacytoma cell line RPMI 8226 was derived from a patient suffering from multiple myeloma. Matsuoka et al (1967) *Proc. Soc. Exp. Biol.* (N.Y.) 125:1246. It can be obtained from the American Type Culture Collection (ATCC), Rockville, Md. under ATCC Deposit No. CCL 155. The lymphoblastoid cell line GM-1500 can be obtained from the Human Genetic Mutant Cell Repository, Institute for Medical Research, Camden, N.J.

In order to assist the selection of successful hybrids, the mutant cell must express a combination of selectable phenotypes. As used in the specification and claims, the phrase "selectable phenotype" refers to a sensitivity or susceptibility to a selective pressure or a lack thereof which can either be complemented or transmitted upon fusion. In particular, the mutant cell must exhibit a first selectable phenotype that can be complemented upon fusion with said other cell and a second selectable phenotype that can be transmitted upon fusion with said other cell. The present invention, however, is not limited to a specific trait for either of said first and second selectable phenotypes and any selectable characteristic can be employed.

Successful hybrids inherit the selectable phenotype capable of being transmitted from the appropriate parent exhibiting that trait while the other selectable phenotype is comlemented upon fusion. As a result, successful hybrids can be isolated by applying appropriate selective pressures to the fusion culture. Non-hybridized parent cells die in the presence of one of the two selective pressures. An isolated hybrid then can be clonally expanded to produce a hybrid cell line.

One widely used selectable phenotype that can be complemented upon fusion is 6-thioguanine resistance. 6-thioguanine resistance is a recessive trait which is complemented upon fusion with a 6-thioguanine sensitive cell line. Cells with this trait are deficient in the enzyme hypoxanthine phosphoribosyl transferase (HPRT) and die in medium containining hypoxanthine, amniopterine, and thymidine (HAT). In other words, cells possessing this trait exhibit HAT sensitivity. One procedure for producing a HAT sensitive cell line is described in (1975) *Nature* 256:495–497.

An alternate selectable phenotype capable of being completed upon fusion is 8-azaguanine resistance. Cells which successfully multiply in 8-azaguanine also are HPRT deficient and therefore HAT sensitive. Still another recessive trait that may be used is thymidine kinase deficiency. Thymidine kinase deficient cells are also HAT sensitive. Other suitable selective phenotypes capable of being complemented upon fusion will be apparent to one skilled in the art.

A known selectable phenotype that is transmitted upon fusion, i.e., inherited by successful hybrids, is ouabain resistance. Ouabain resistance is an autosomal dominant trait. Ouabain sensitive cells die in the presence of ouabain. A technique for producing a cell line resistant to ouabain is described in (1982) *Proc. Natl. Acad. Sci. U.S.A.* 79:6651–6655. Another selectable phenotype capable of being transmitted upon fusion is resistance to antibiotic G-418. A cell line having a dominant marker conferring resistance to the antibiotic G-418 can be obtained by transfection of the cell with DNA carrying a bacterial gene for neomycin resistance. See e.g., Teng et. al., (1983) *Proc. Natl. Acad. Sci. U.S.A.*, 80: 7308–7312. Other possible selectable phenotypes capable of being transmitted to successful hybrids upon fusion will appear to one skilled in the art.

For example, a mutant cell of the human B lymphoblastoid cell line GM-1500 exhibiting a combination of selectable phenotypes has been prepared using the following procedure. A cell obtained from the GM-1500 cell line first was mutated by chemical treatment with ethyl methyl sulfonate and selected for HPRT deficiency in medium containing 6-thioguanine. One of the HPRT-deficient mutants obtained, designated GM-1500 6TG A-1 1 then was clonally expanded and a clone thereof was mutated with low level gamma irradiation followed by selection for ouabain resistance and subsequent cloning. Kozbor et al, (1982) *Proc. Natl. Acad. Sci. U.S.A.* 79:6651. The resulting cell line has been designated KR-4 and this cell line is available from the Department of Microbiology and Immunology, Queen's University, Kingston, Ontario, Canada K7L 3N6. This lymphoblastoid cell line exhibits both ouabain resistance and 6-thioguanine resistance and can be used as the mutant cell for preparing a somatic cell hybrid in accordance with the present invention.

The somatic cell hybrid of this invention then is prepared by fusing a mutant cell obtained from one of eitehr the human lymphoblastoid cell line GM-1500 or the human plasmacytoma cell line RPMI 8226 with a cell obtained from the other of either the GM-1500 cell line or the RPMI 8226 cell line. Techniques for hybridizing or fusing cells are well known in the art, see, e.g., Kohler and Milstein, *Nature*, 205:495 (1975). In accordance with such techniques, the hybridization or fusion step for preparing the somatic cell hybrid of this invention employs a large number of the mutant cells obtained from either the plasmacytoma cell line RPMI 8226 or the lymphoblastoid cell line GM-1500 and a large number of cells obtained from the other of either the RPMI 8226 cell line or the GM-1500 cell line. Typically, the cells are mixed, centrifuged and resuspended for fusion in a solution of polyethylene glycol (PEG) diluted in growth medium. Fused cells then are washed and cultured. This procedure typically yields only a relatively small number of successful cell hybrids.

Since one of the parental cell lines has been appropriately mutated to introduce a combination of selectable phenotypes, one phenotype capable of being complemented upon fusion and the other phenotype capable of being transmitted to or inherited by the hybridized cells, it is possible to isolate successful hybrids from the non-hybridized parents using the appropriate selective presures. For example, when fusing plasmacytoma cells, RPMI 8226, with lymphoblastoid cells, KR-4, the 6-thioguanine resistance of the lymphoblastoid cell is complemented upon fusion while the ouabain resistance of the lymphoblastoid cell is transmitted to successful hybrids. Successful hybrids therefore can be isolated by culturing the fusion products in medium containing HAT and ouabain since only hybrid cells can survive in such medium. The non-hybridized lymphoblastoid cells die in the presence of HAT while the non-hybridized plasmacytoma cells die in the presence of ouabain.

In order to produce a somatic cell hybrid suitable for fusion with antibody producing cells which can be isolated from both parental cells, it is necessary to selectively mutate the cell hybrid produced above so that the resulting somatic cell hybrid exhibits a selectable phenotype capable of being complemented upon fusion with an antibody producing cell. For convenience, the same selective pressure used in isolating the above-described somatic cell hybrid can be employed, i.e., 6-thioguanine resistance although a different selectable phenotype could be used if so desired. The cells can be mutated by any known physical or chemical treatment technique followed by selection in an appropriate medium, e.g., a medium containing 6-thioguanine when obtaining a HAT sensitive mutant.

In the case of a somatic cell hybrid produced from a cell hybrid prepared by fusing the KR-4 lymphoblastoid cells with the RPMI 8226 plasmacytoma cells, it has been found that suitable mutants are produced spontaneously simply by culturing a previously isolated cell hybrid in medium containing 6-thioguanine and ouabain.

While the present invention has specifically been illustrated using a mutant cell obtained from the lymphoblastoid cell line GM-1500 to obtain the first cell hybrid, in the broad practice of this invention a mutant cell exhibiting the required combination of selectable phenotypes can alternately be prepared by mutating the plasmacytoma cells RPMI 8226. This mutation can be effected using any suitable mutation technique that does not otherwise adversely affect the cell.

Since upon fusion, the somatic cell hybrid of this invention generally is hypotetraploid, the hybrid must stabilize at a chromosone number without loss of desired traits.

The following examples are provided for illustrative purposes only and ar not intended to limit the scope of the invention.

EXAMPLE 1

This example describes the production of a 6-thioguanine-resistant and ouabain-resistant hybrid cell line suitable as a fusion partner for production of monoclonal antibodies by fusing plasmacytoma cells RPMI 8226 and human lymphoblastoid cells KR-4. As noted above, the KR-4 cell line was derived from the lymphoblastoid line GM 1500. Cells of the human lymphoblastoid cell line KR-4, were maintained in culture medium containing 0.1 mM ouabain and 30 micrograms per milliliter 6-thioguanine (6-TG). Cells of the plasmacytoma cell line, RPMI 8226, were maintained in RPMI 8226 medium containing 10% heat-inactivated fetal calf serum, 2 mM L-glutamine and 60 micrograms per milliliter gentamicin.

Hybrids of cells obtained from the lymphoblastoid cell line KR-4 and the plasmacytoma cell line RPMI 8226 were prepared by mixing and centrifuging about 10 million plasmacytoma cells with 10 million lymphoblastoid cells. This cell mixture was centrifuged at $150 \times g$ for about 10 minutes and the cells were fused using 45% (w/v) of polyethylene glycol-4000 (PEG) diluted in RPMI medium using the procedure essentially described by Kohler, G. and C. Milstein (1975) *Nature* 256:495.

Fused cells were washed and then cultured in wells of microtiter plates (Linbro) by seeding about 10,000 cells per well on irradiated (3000R) mouse spleen cells (about 5,000 cells per well) as feeders. The cells were cultured sequentially in HAT medium containing 10 mM of ouabain for the first two weeks, 100mM hypoxanthine/16 mM thymidine for the next week, and finally RPMI 1640 medium containing 20% fetal calf serum. Control cultures containing each of the parental cell lines contained no survivors after 12 days in the medium containing HAT and ouabain.

Successful hybrids then were back-selected for 6-thioguanine resistance and ouabain resistance merely by culturing the identified hybrids in medium containing 30 micrograms per milliliter of 6-thioguanine and 0.1 mM of ouabain.

All hybids secreted both kappa and lambda immunoglobulin chains as determined by immunoprecipitation with 35S-methionine-labelled immunoglobulin as well as class IgG antibody. The hybrids had a growth rate intermediate between the two parental cell lines exhibiting a doubling time of 24–28 hours. One of the hybrids designated KR-12 has been deposited with the American Type Culture Collection (ATCC), 12301 Parklawn Drive, Rockville, Md. 20852, on Oct. 31, 1984, 1984, and can be obtained under Deposit No. CRL-8658.

This particular cell line exhibits a successful fusion frequency of about $8 \times 10^{-7}$ with normal peripheral blood lymphocytes and shows a frequency of hybrid formation on the order of about $10^{-5}$ with an antibody producing lymphoblastoid cell line immortalized by treatment with Epstein-Barr virus (EBV). These fusion frequencies are comparable to those of the KR-4 lymphoblastoid parental cell line. KR-12 cells express both intracellular and surface immunoglobulin (gamma heavy chain, and lambda and kappa light chains), secrete immunoglobulin in amounts 15 times that of the parental cells and possess the morphological characteristics of the plasmacytoma parent.

EXAMPLE 2

This example describes the production of hybrids formed by fusing the KR-12 cells obtained in accordance with Example 1 with antibody-producing cells secreting antibody specific for a known antigen. In this example, a lymphoblastoid cell line B6, which secrets IgM antitetanus toxoid antibody was used. The B6 cell line was derived from peripheral blood lymphocytes of an immunized donor following selection for antigen-specific B cells, transformed with Epstein-Barr virus and subsequently cloned, see Kozbor, D. and J. C. Roder (1981) *J. Immunol.*, 126 (4):1275. The fusion procedure outlined in Example 1 was employed and hybrids were selected in HAT medium supplemented with 10 mM ouabain.

The hybrid formation frequency 20 days after selection was estimated as $10^{-5}$ by scoring the fraction of negative wells and applying Poisson's equation. Control plates containing each of the parental cell lines cultured in the same medium as used to select hybrids exhibited no survivors.

All of the hybrids secreted between 5 to 30 micrograms per milliliter of IgG and IgM antibodies but only IgM kappa had specificity for tetanus toxoid as determined by enzyme-linked immunosorbent assay, see Engvall, E. and P. Perlmann (1971) *Immunochemistry* 8:871.

The hybrid cells were cloned in wells of Linbro plates by limiting dilution on a feeder layer consisting of irradiated (3,000 R) mouse spleen cells and separate clones were tested for antibody production. The cloning efficiency was about 54%. Three representative clones, designated HYBA-1, HYBA-2 and HYBA-3 produced 7, 8, 8 micrograms per milliliter of IgG antibody and 9, 8, 10 micrograms per milliliter of IgM antibody, respectively, at the end of an 8 day growth period. The hybrids produced 10 times more IgM than the B6 parental cell. The hybrid clones continue to sustain the same level of immunoglobulin production through 12 months of continuous culture.

EXAMPLE 3

In an attempt to increase antibody production, the anti-tetanus toxoid antibody-producing hybrids were grown in the peritoneal cavity of pristane-primed nude mice. Hybrids were adopted for ascites growth in the nude mice after a single passage as a solid subcutaneous tumor in irradiated nude mice (350 R) followed by growth in vitro. Additionally, in two out of eight irradiated mice, it was possible to obtain ascites growth of hybrids without previous growth as solid tumors. The hybrids secreted one to eight milligrams of human immunoglobulin per milliliter of ascites fluid. This level of human immunoglobulin yield was about 10 times higher than the yield obtained by ascites growth of antibody producing hybrids prepared from the B6 cell line and the KR-4 lymphoblastoid cell line. While most irradiated mice developed ascites fluid after injection of hybrid cells, only small quantities of ascites fliud, i.e., on the order of 0.5 and 2.0 ml, were obtained per mouse.

While preferred embodiments of this invention have been described herein, those skilled in the art will appreciate that changes and modifications may be made without departing from the spirit and scope of the invention, as defined in and limited only by the scope of the appended claims.

We claim:

1. A stable, continuous human somatic cell hybrid cell line produced by fusing a mutant cell obtained from one of either the human plasmacytoma cell line RPMI 8226 or the human lymphoblastoid cell line GM 1500 with a cell obtained from the other of either the RPMI 8226 cell line or the GM-1500 cell line, to produce a first hybrid cell line, said mutant cell exhibiting a first selectable phenotype capable of being complemented and a second selectable phenotype capable of being transmitted upon fusion with said other cell, and then mutating a cell of said first hybrid cell line to obtain said human somatic cell hybrid cell line exhibiting a selectable phenotype that can be complemented upon fusion with an antibody producing cell and having the ability to form a stable continuous cell line upon fusion with an antibody producing cell.

2. The hybrid cell line of claim 1 wherein said first selectable phenotype is 6-thioguanine resistance.

3. The hybrid cell line of claim 1 wherein said second selectable phenotype is ouabain resistance.

4. The hybrid cell line of claim 1 which cannot survive in media containing hypoxanthine, aminopterin and thymidine.

5. The hybrid cell line of claim 1 wherein said mutant cell is obtained from the human lymphoblastoid cell line GM 1500.

6. The hybrid cell line of claim 5 produced by fusing cells of the human plasmacytoma cell line RPMI 8226 with mutant cells of the human lymphoblastoid cell line GM 1500 having 6-thioguanine and ouabain resistances.

7. A hybridoma cell line clonally derived from a hybridoma produced by the fusion of an antibody producing cell and a cell from the human somatic cell hybrid cell line of claim 6.

8. A hybridoma cell line clonally derived from a hybridoma produced by the fusion of an antibody producing cell and a cell from the human somatic cell hybrid cell line of claim 1.

9. A hybridoma cell line of claim 8 wherein said antibody producing cell is a B lymphocyte immortalizied by treatment with Epstein-Barr virus.

10. A hybridoma cell line of claim 8 wherein said antibody producing cell is a normal B lymphocyte.

11. A method for forming a stable, continuous human somatic cell hybrid cell line useful as a fusion partner for antibody producing cells comprising fusing a mutant cell obtained from one of either the human plasmacytoma cell line RPMI 8226 or the human lymphoblastoid cell line GM-1500 with a cell obtained from the other of either the RPMI cell line or the GM-1500 cell line to produce a first hybrid cell line, said mutant cell having a first selectable phenotype that can be complemented and a second selectable phenotype that can be transmitted upon fusion with said other cell line and then mutating said first hybrid cell to obtain said human somatic cell hybrid cell line exhibiting a selectable phenotype that can be complemented upon fusion with an antibody producing cell and having the ability to form a stable continuous cell line upon fusion with an antibody producing cell.

12. A method for forming a hybridoma comprising fusing an antibody producing cell with a cell obtained from the human somatic cell hybrid cell line of claim 1 to obtain a cell hybrid of said antibody producing cell and said human somatic cell hybrid.

* * * * *